United States Patent [19]
Buckley et al.

[11] Patent Number: 5,522,868
[45] Date of Patent: Jun. 4, 1996

[54] METHOD AND APPARATUS FOR DETERMINATION OF PSORALEN CONCENTRATIONS IN BIOLOGICAL TISSUES

[75] Inventors: Lisa A. Buckley; Scott A. Prahl, both of Portland, Oreg.; Steven L. Jacques, Houston, Tex.

[73] Assignee: Sisters of Providence in Oregon, Portland, Oreg.

[21] Appl. No.: 294,475

[22] Filed: Aug. 23, 1994

[51] Int. Cl.$^6$ .................................................. A61B 5/00
[52] U.S. Cl. ........................................ 607/94; 128/633
[58] Field of Search ................ 128/633–4, 664–6; 356/41; 250/483.1; 607/88–95

[56] References Cited

U.S. PATENT DOCUMENTS

| | | | |
|---|---|---|---|
| 4,545,987 | 10/1985 | Giles et al. | 424/89 |
| 4,558,700 | 12/1985 | Mutzhas | 607/94 |
| 5,116,864 | 5/1992 | March et al. | 514/455 |
| 5,344,433 | 9/1994 | Talmore | 607/88 |

OTHER PUBLICATIONS

Gasparro, F., et al., *Journal Investigative Dermatology* 90, 234–236 (1988).

Schomacker, Kevin T., et al., "Ultraviolet Laser–Induced Fluorescence of Colonic Tissue: Basic Biology and Diagnostic Potential", *Lasers in Surgery and Medicine* 12:63–78 (1992).

*Primary Examiner*—Angela D. Sykes
*Assistant Examiner*—Robert L. Nasser, Jr.
*Attorney, Agent, or Firm*—Nixon & Vanderhye

[57] ABSTRACT

Levels of psoralen concentration in a biological detection target are determined so that an appropriate UVA light dose of PUVA therapy can be delivered to a biological treatment target. The appropriate therapy is determined by the product of the UVA light dose and psoralen concentration level. After determination of a baseline optical autofluoresence signal from the detection target, a first dosage of psoralen (preferably 8-methoxypsoralen [8-MOP]) is administered. Thereafter, the detection target is irradiated under the same conditions as the pre-psoralen irradiation. Then, the optical return from the psoralen-treated detection target is analyzed. A computer (86) compares the pre-psoralen optical return and psoralen-treated optical return to calculate a real time determination of the concentration level of psoralen in the treatment target. Then, then knowing the precise psoralen concentration level, a UV dosage level required to achieve the desired PUVA therapy can be precisely determined and applied to the treatment target. In some embodiments, the detection target is the treatment target and in vivo real time psoralen concentration is determined. Various forms of applicators (52, 452, 552, 652, 752) are provided for differing types of targets. Each applicator is mounted on an optical fiber bundle (54). In some embodiments, the same optical fiber bundle (54) is employed to transmit the irradiation and optical return signals in the psoralen concentration determination, as well as to transmit the UVA for the PUVA therapy.

45 Claims, 10 Drawing Sheets

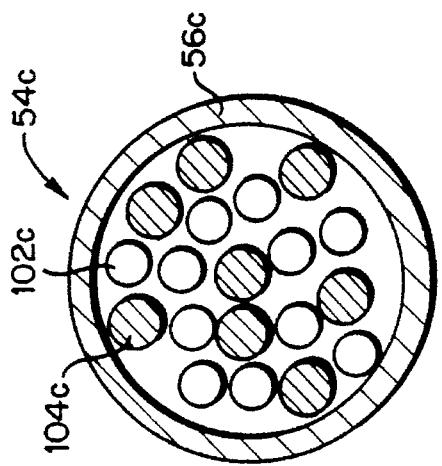
FIG. 3C
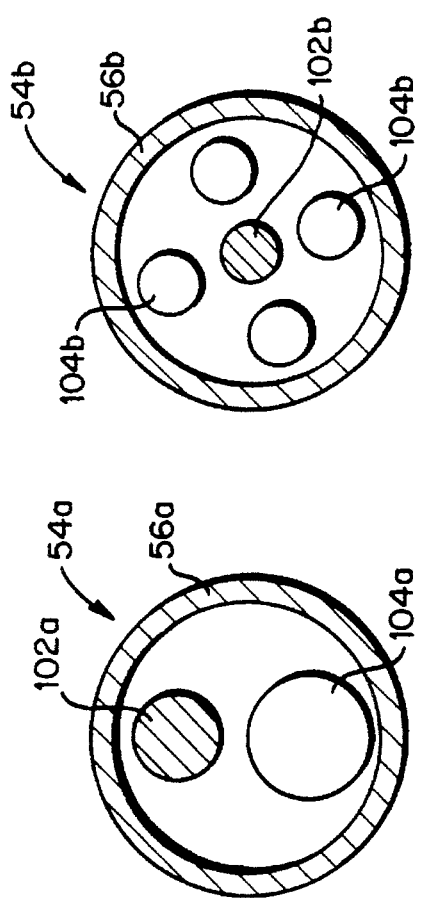
FIG. 3B
FIG. 3A
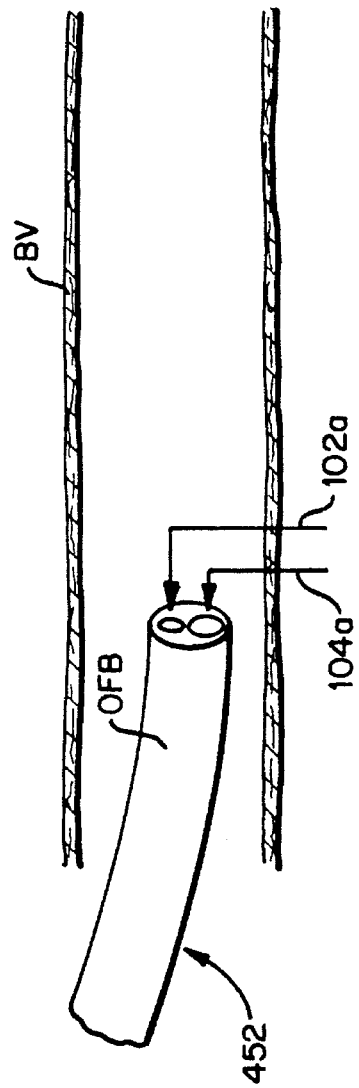
FIG. 4

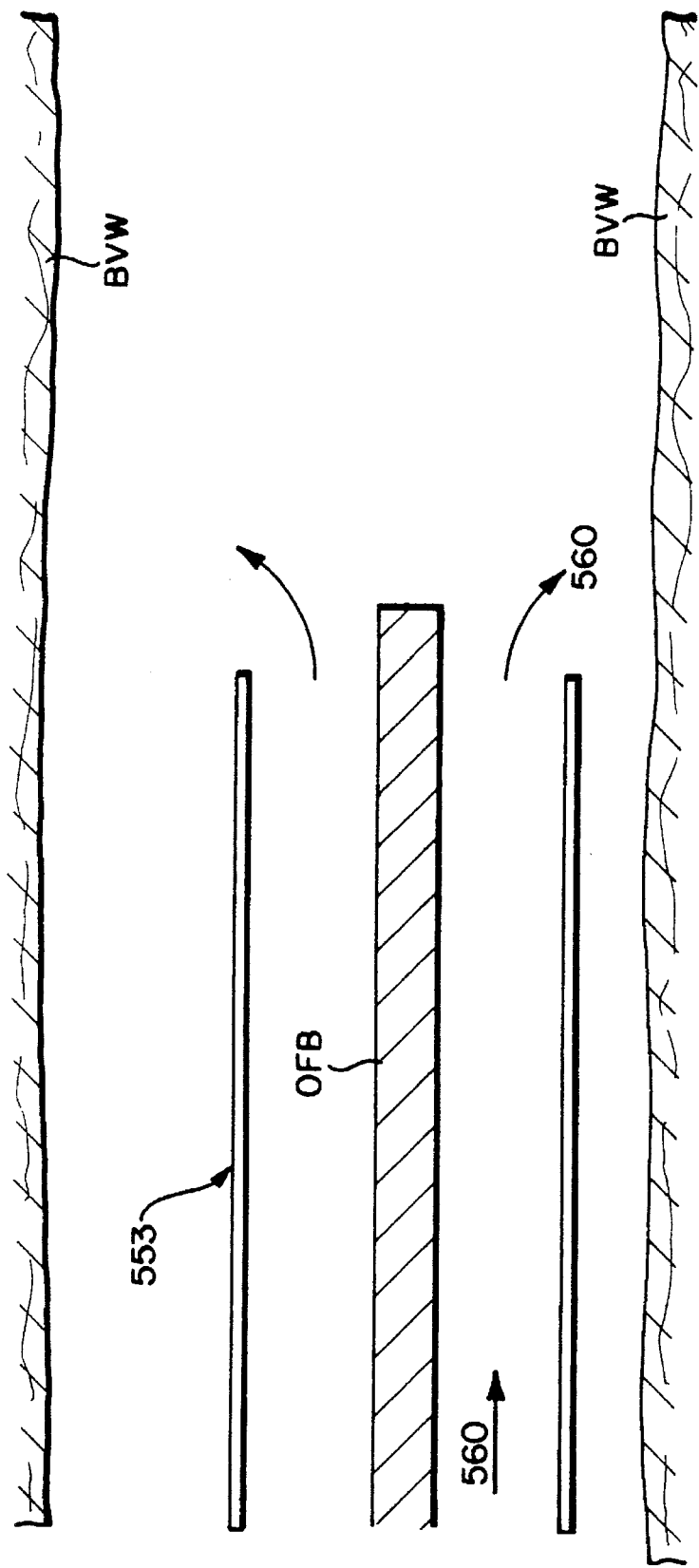

5,522,868

METHOD AND APPARATUS FOR DETERMINATION OF PSORALEN CONCENTRATIONS IN BIOLOGICAL TISSUES

BACKGROUND

1. Field of Invention

This invention pertains to the proper dosimetry of UV light in clinical applications involving psoralen (e.g., PUVA therapy).

2. Related Art and Other Considerations

Psoralen concentrations in biological tissues are required for proper dosimetry of ultraviolet (UV) light in many clinical applications involving psoralen. As an example of one such application, PUVA therapy (Psoralen administration followed by Ultraviolet A irradiation) may prove effective in preventing restenosis of vessels following balloon angioplasty to open vessels narrowed by atherosclerosis. This technique relies on the ability of PUVA to cause crosslinks and monoadducts that prevent cellular proliferation without causing cell death. See, for example, U.S. patent application Ser. No. 08/041,001, filed Mar. 29, 1993 by Kenton W. Gregory, entitled "Inhibiting Vascular Smooth Muscle Cell Proliferation"; U.S. patent application Ser. No. 07/781,996, filed Oct. 23, 1991, by Kenton W. Gregory and R. Rox Anderson, entitled "Laser-Based Inhibition of Smooth Muscle Cell Hyperproliferation"; and U.S. Pat. No. 5,116,864 issued to March et al. (all of which are incorporated herein by reference).

Typically, the efficacy of PUVA therapy depends on the psoralen concentration and the UV dosage (e.g., the product of light dose and psoralen level). Variations in psoralen drug levels can lead to sub-optimal treatment.

Previous methods for determining psoralen levels are not real time determinations. Moreover, such methods are cumbersome for use in clinical PUVA applications and require elaborate equipment. Traditionally, such methods involve reverse phase liquid chromatography of blood serum. See, for example, Gasparro, F., et al., *Journal Investigative Dermatology* 90, 234–236, 1988. In such methods, the psoralen is physically separated from the tissue components and psoralen absorption is used to quantify levels of psoralen concentration.

SUMMARY

Levels of psoralen concentration in a biological detection target are determined so that an appropriate UVA light dose can be delivered to a biological treatment target undergoing PUVA therapy. The appropriate therapy is determined by the product of the UVA light dose and psoralen concentration level. The targets can be any phyisological component including serum, blood and its components, a blood vessel wall, skin, or other tissue (e.g., tissue surrounding a blood vessel; organs including transplanted organs).

In a first mode, psoralen concentration for a subject is determined with reference to an actual biological target (e.g., treatment target) which eventually is to be treated with the PUVA therapy. In such first mode, an applicator is situated/installed proximate tissue which serves both as a detection target and a treatment target. In a second mode, tissue (e.g., blood) is extracted from the subject to serve as a detection target and is placed in an appropriate in vitro container. Psoralen concentration is determined by positioning a first applicator proximate the container, and then emitting the appropriate amount of UVA using a second applicator positioned/installed proximate the treatment target. Thus, in the first mode, the detection target and the treatment target can be one and the same, which is not the case for the second mode.

After installation of an applicator, but before administering of the psoralen, the detection target is irradiated to obtain an optical autofluoresence and thereby establish a baseline reading. Preferably the irradiation light has an excitation wavelength in a range from about 340 nm to about 400 nm, and is more preferably about 365 nm. The autofluoresence signal is monitored at a detection station, preferably in a range of from 400 nm to 700 nm.

After determination of the optical autofluoresence signal from the detection target, a first dosage of psoralen (preferably 8-methoxypsoralen [8-MOP]) is administered to the subject. Thereafter, the detection target (extracted from the subject for in vitro modes) is irradiated under the same conditions as the pre-psoralen irradiation. Then, the optical return from the psoralen-treated detection target is analyzed at the detection station in the same range as the autofluoresence signal. Since psoralen absorbs light and can fluoresce, the presence of psoralen in the detection target changes the light returned by the detection target. These changes are used to quantify the psoralen levels in the detection target.

A computer at the detection station compares the pre-psoralen optical return and psoralen-treated optical return to calculate a concentration level of psoralen in the detection target. Then, if a sufficient concentration of psoralen has not been detected over an adequate time period, a further administering of psoralen can occur. If the level of psoralen concentration is determined to be sufficient, then knowing the precise psoralen concentration level, a UV dosage level required to achieve the desired PUVA therapy can be precisely determined and applied to a treatment target.

Various forms of applicators are provided for differing types of targets. The applicator is mounted on an optical fiber bundle. In some embodiments, the same optical fiber bundle is employed to transmit the irradiation and optical return signals in the psoralen concentration determination, as well as to transmit the UVA for the PUVA therapy.

BRIEF DESCRIPTION OF TEE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

Figure 1:
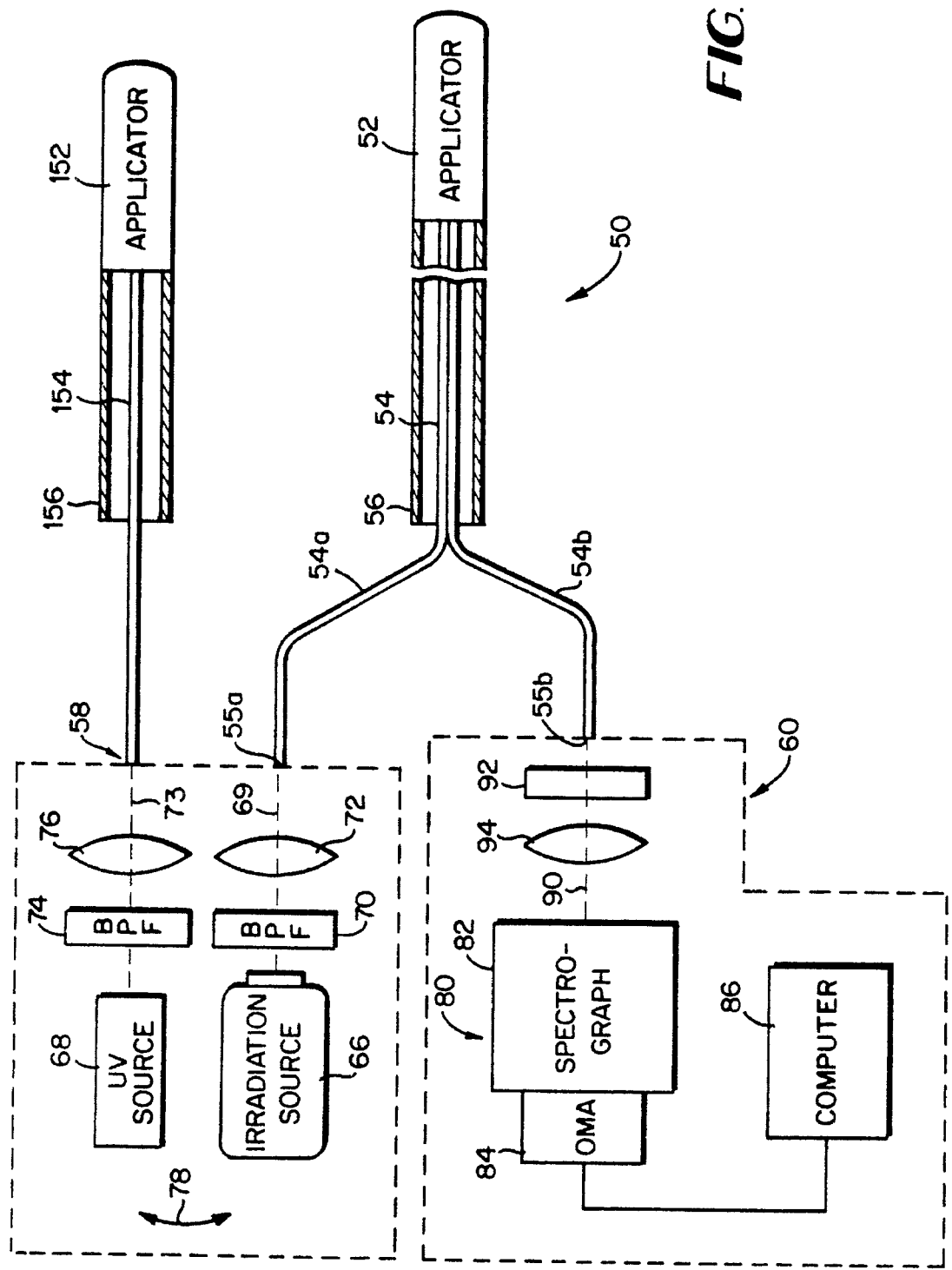
FIG. 1 is a schematical diagrammatic view of a system for in vivo determination of psoralen levels and UV treatment according to a first (bifurcated optical fiber bundle) embodiment of the invention.

FIGS. 3A, 3B, and 3C are cross-sectional end views of optical fiber bundles suitable for use in the system of FIG. 1.

FIG. 4 is a diagrammatic view of an applicator for making an in vivo determination of psoralen concentration in blood.

Figure 5:
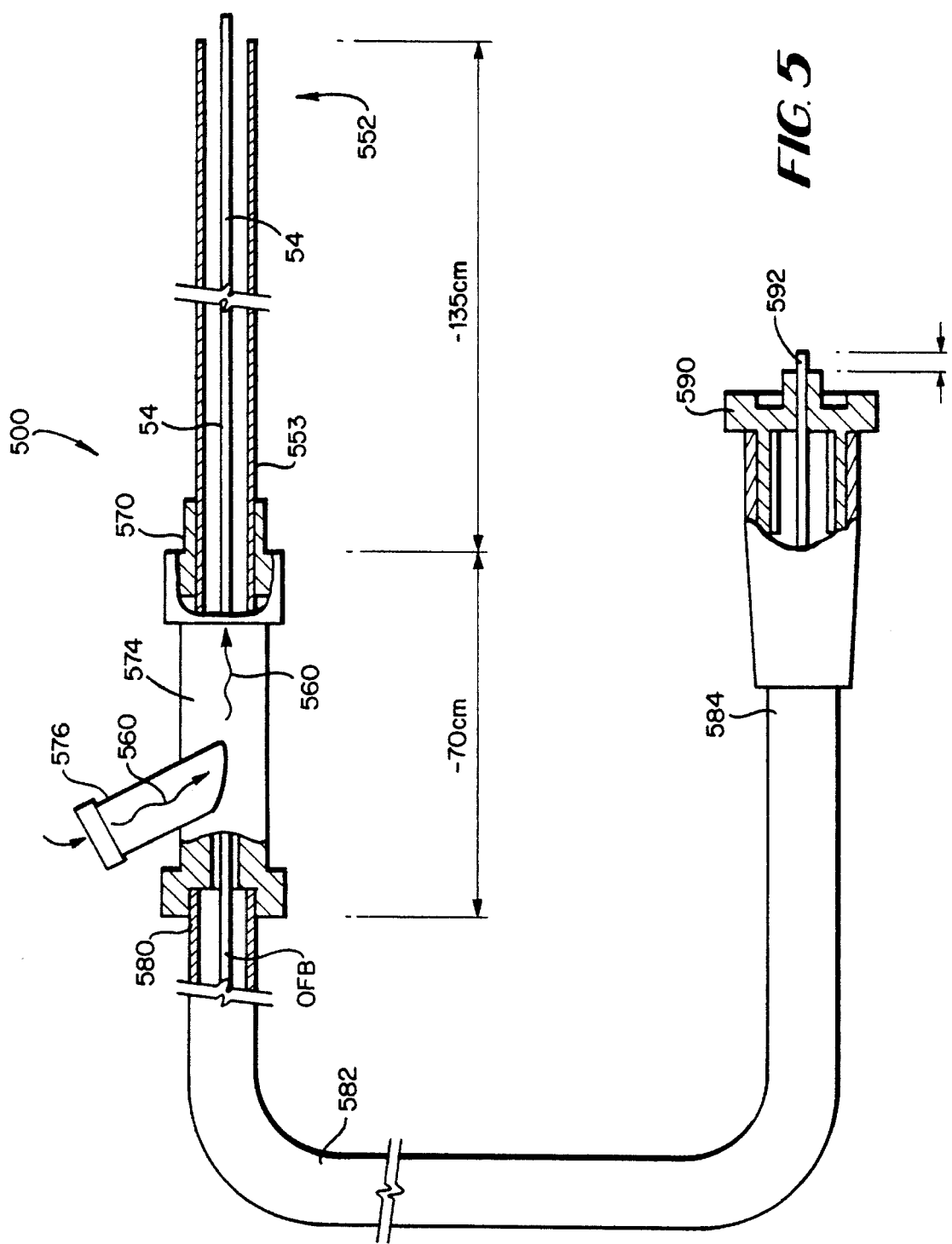

FIG. 5 is a diagrammatic cross-sectional view of an applicator for making an in vivo determination of psoralen concentration in a vessel wall, additionally showing a combined optical and saline flush delivery system.

FIG. 5A is an enlarged diagrammatic cross-sectional view of a distal end of the applicator of FIG. 5.

Figure 6A:
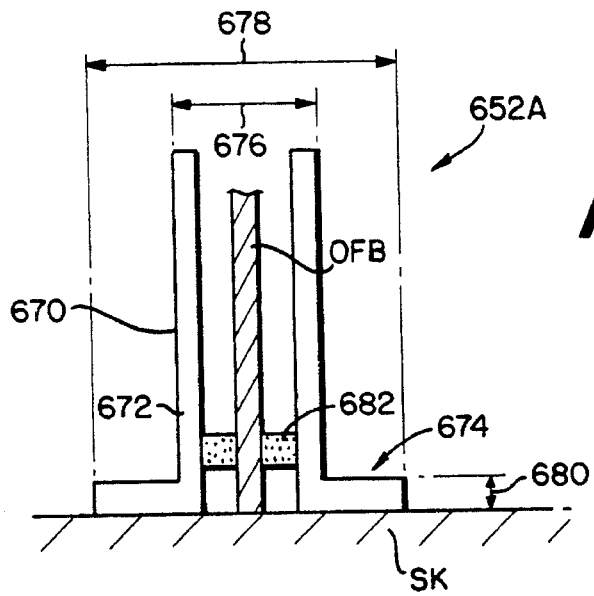
Figure 6B:
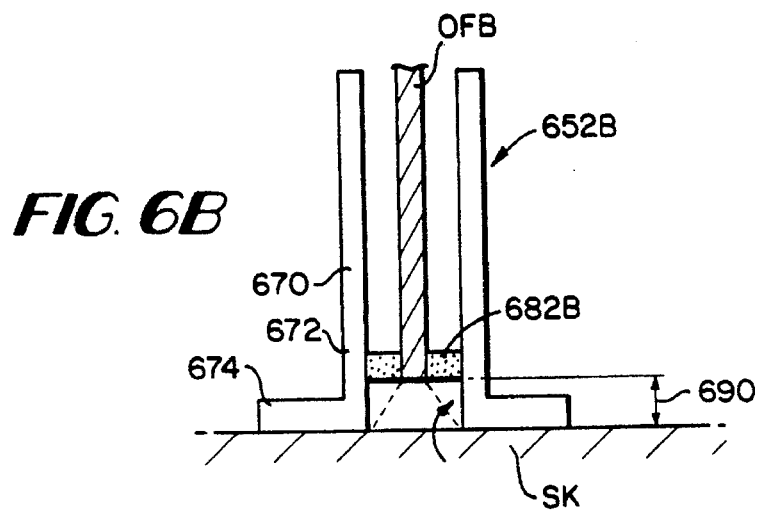

FIG. 6A and FIG. 6B are diagrammatic cross-sectional views of an applicator for making an in vivo determination of psoralen concentration in skin.

Figure 7:
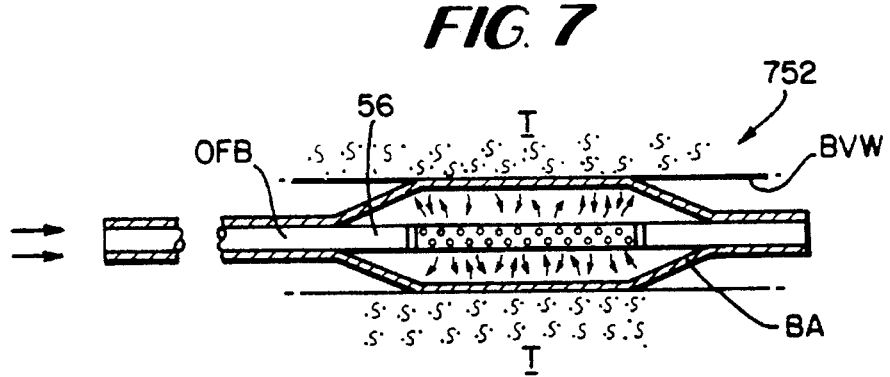

FIG. 7 is a diagrammatic cross-sectional view of balloon light delivery and detection system.

Figure 8:
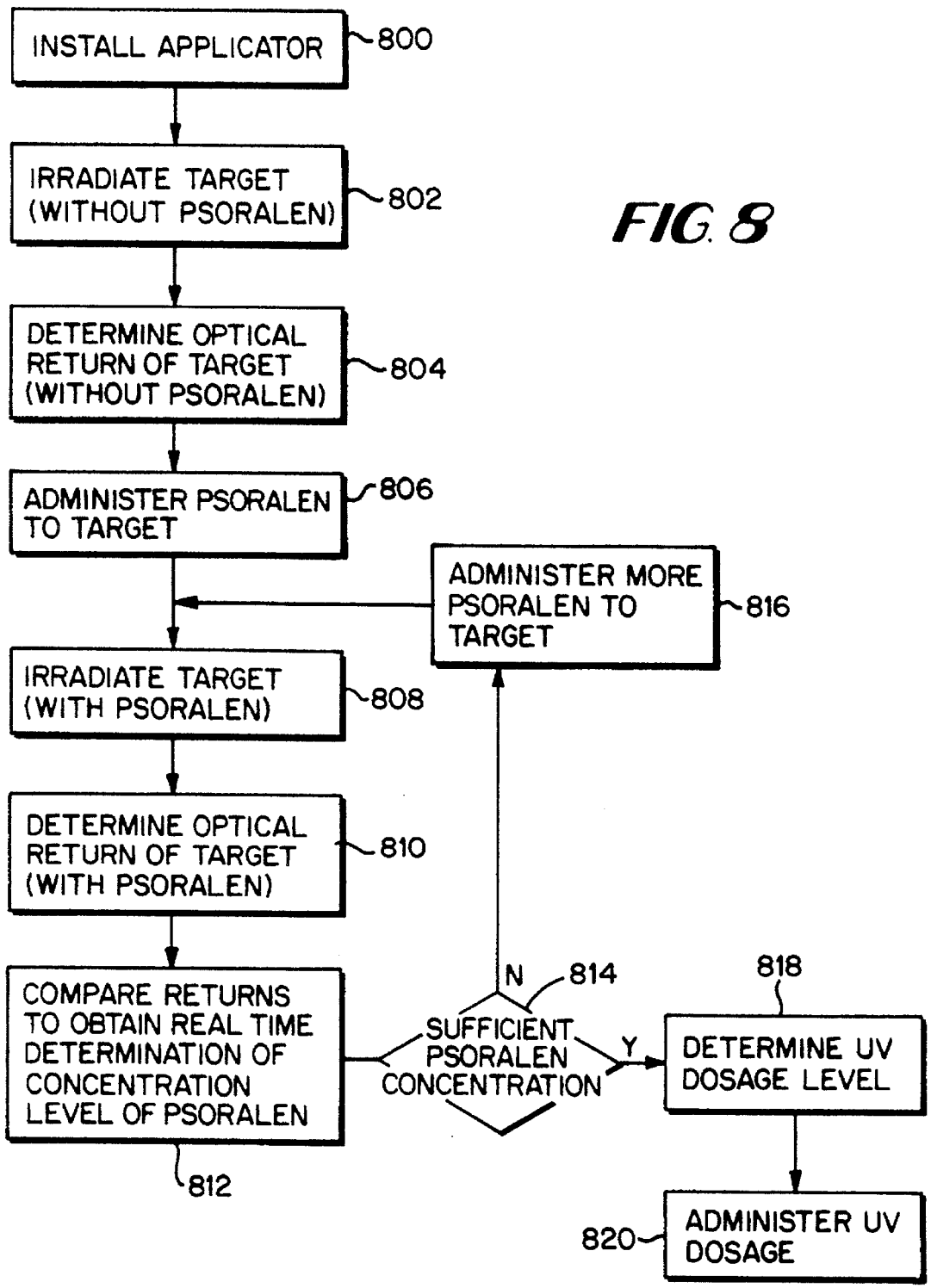

FIG. 8 is a flowchart depicting steps involved in the real-time psoralen concentration determination method of the invention.

Figure 9:
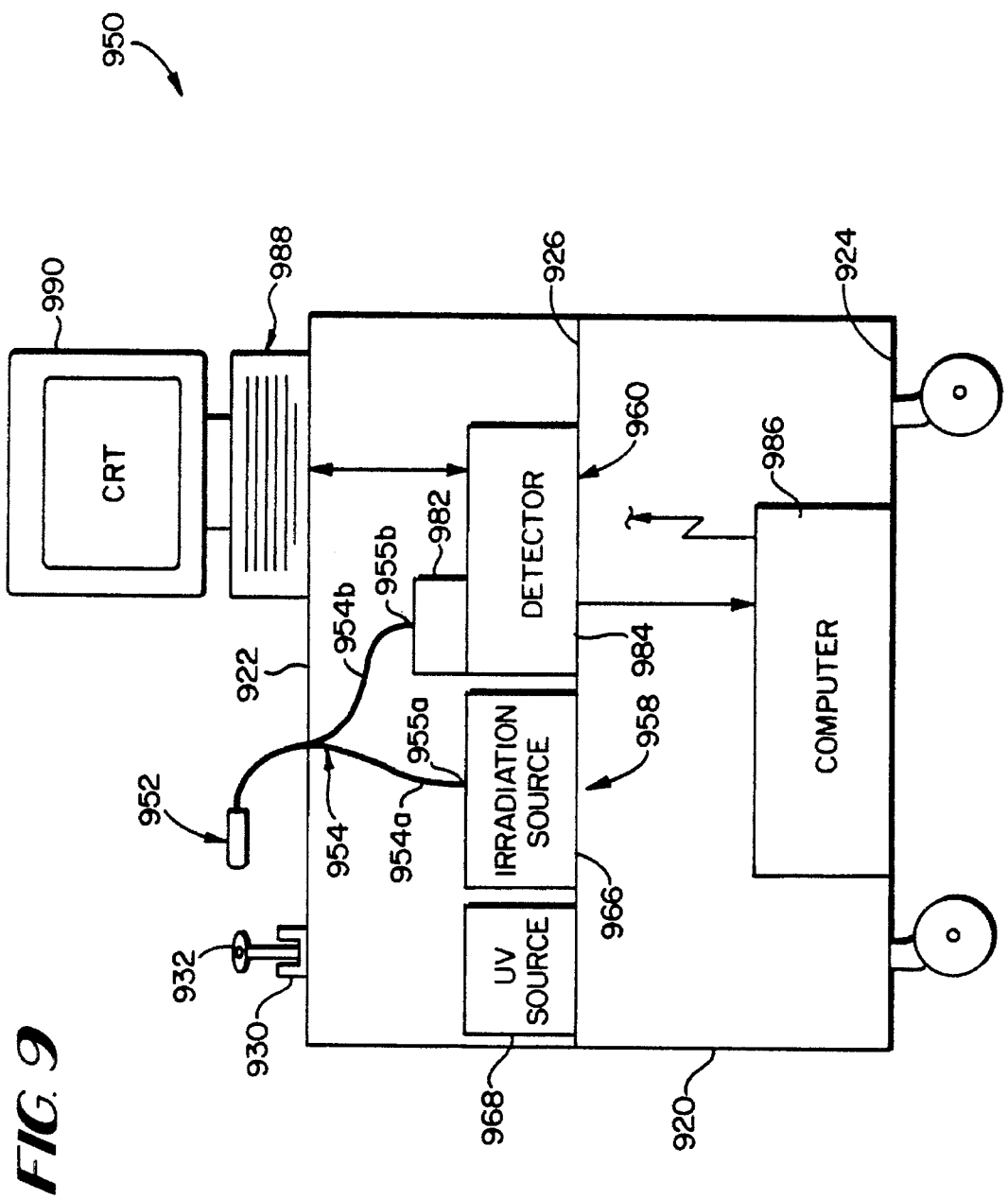

FIG. 9 is a schematical diagrammatic view of a portable psoralen concentration determination system according to an embodiment of the invention.

Figure 10:
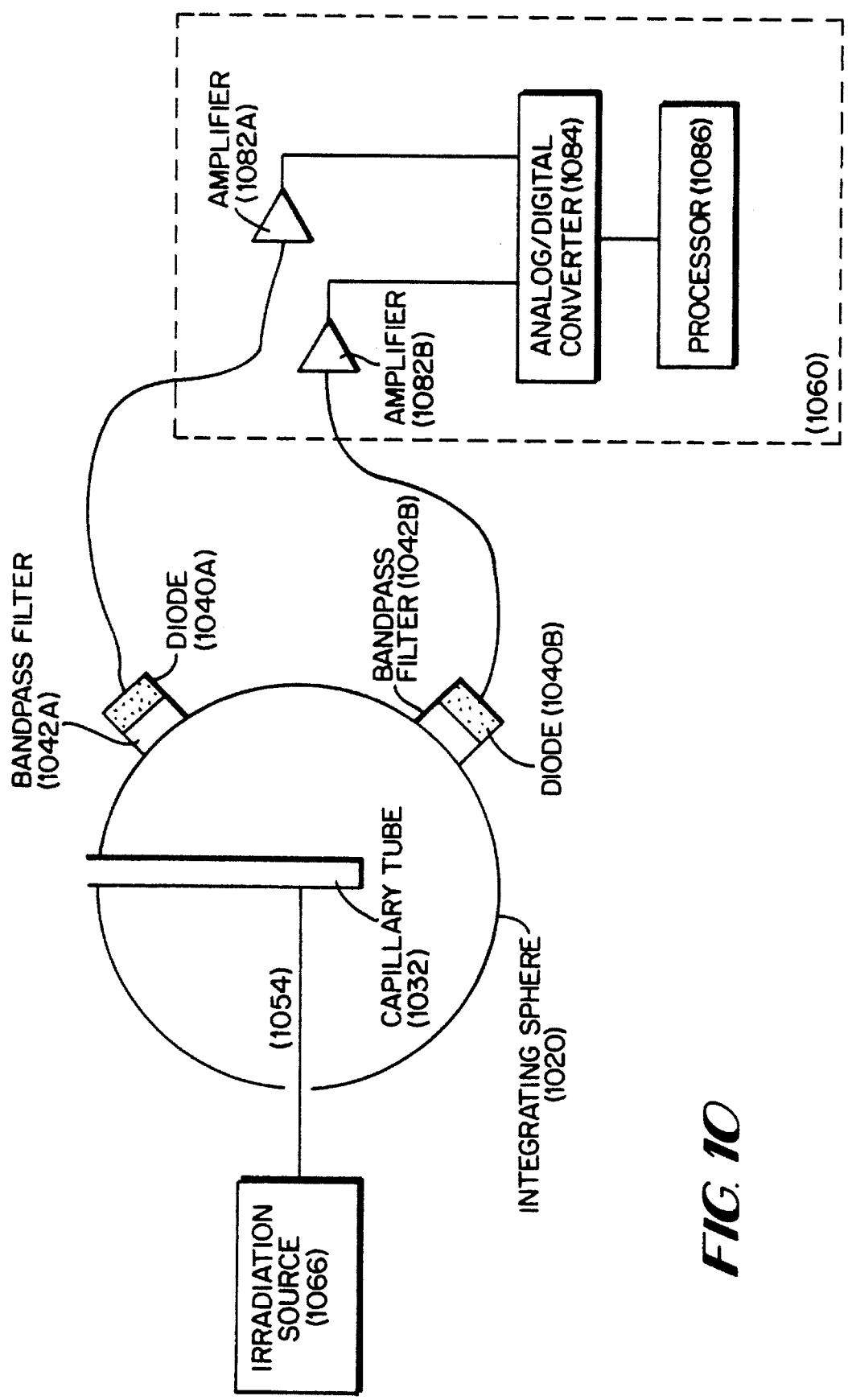

FIG. 10 is a schematical diagrammatic view of a psoralen concentration determination system according to another embodiment of the invention.

Figure 11A:
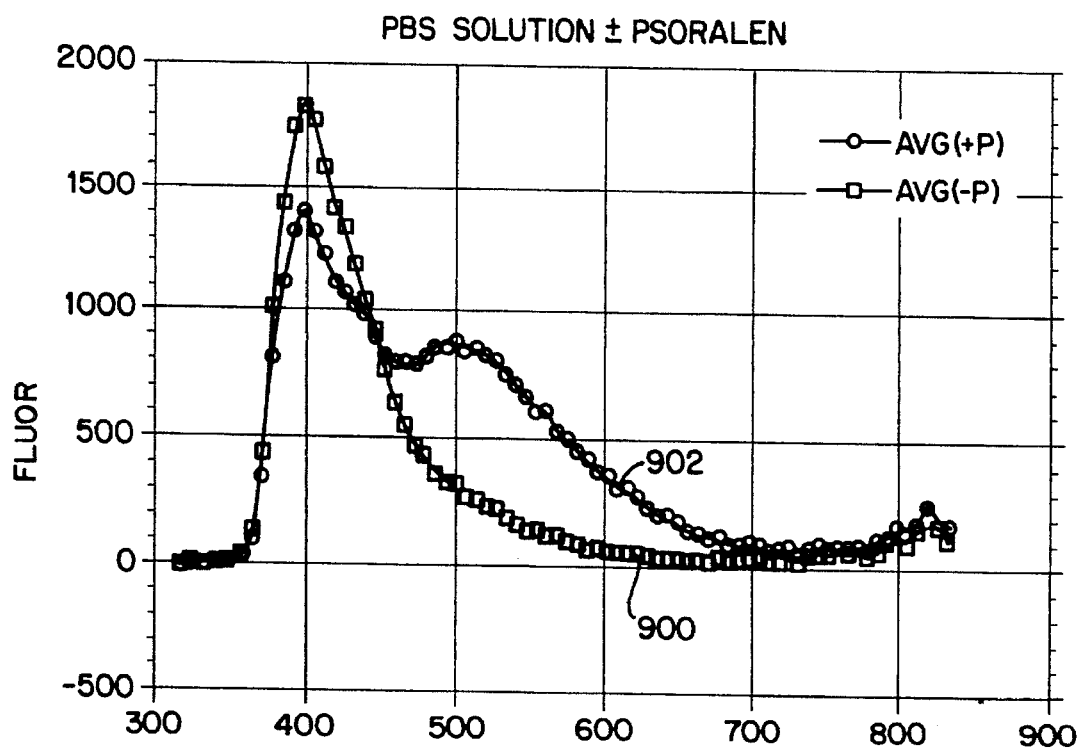

FIG. 11A is a graph showing optical return signals prior to and subsequent to psoralen administration.

Figure 11B:
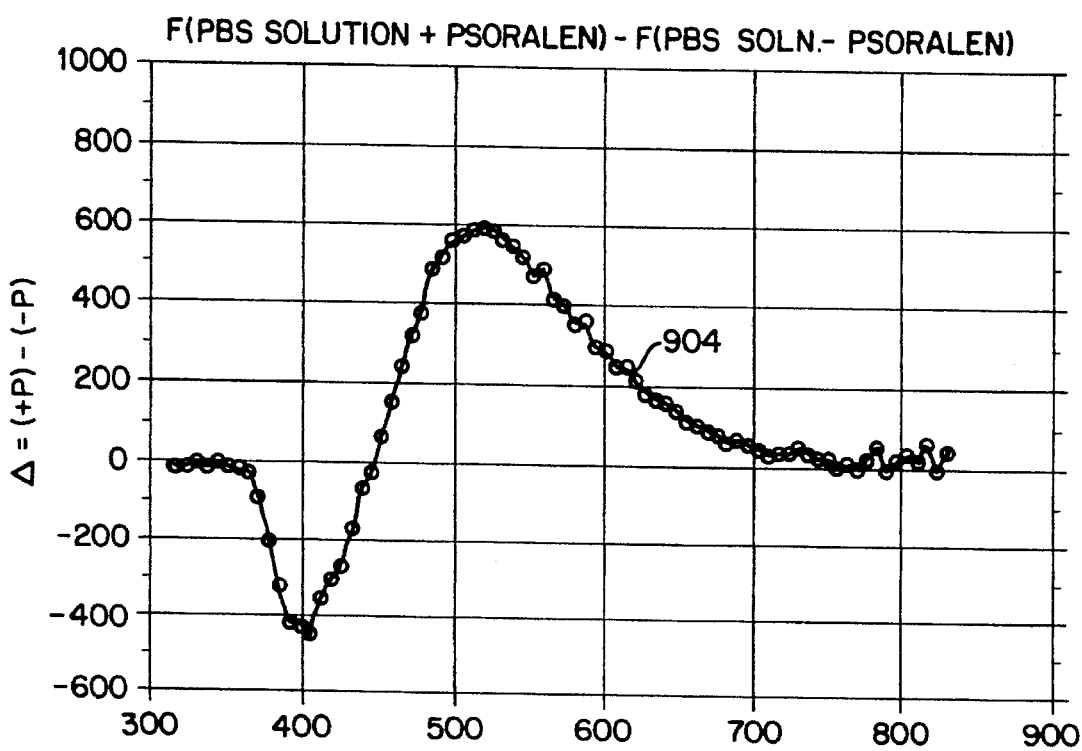

FIG. 11B is a graph showing a difference of the optical return signals of FIG. 11A.

DETAILED DESCRIPTION OF THE DRAWINGS

FIG. 1 shows a psoralen concentration determination and UV treatment system 50 according to a first embodiment of the invention. System 50 includes a first applicator 52 fitted on an end of an optical fiber bundle 54 and a second applicator 152 fitted on an end of optical fiber 154. Optical fiber bundles 54 and 154 have protective (e.g., plastic) coverings 56 and 156, respectively.

In the particular embodiment shown in FIG. 1, optical fiber bundle 54 includes two sub-bundles 54a and 54b. Optical fiber sub-bundle 54a has an end 55a which extends from covering 56 toward a launching station 58; optical fiber sub-bundle 54b has an end 55b which extends from covering 56 toward a detection station 60. Optical fiber bundle 154, upon which applicator 152 is fitted, extends to launching station 58.

In the embodiment shown in FIG. 1, launching station 58 includes two sources of electromagnetic energy, in particular irradiation source 66 and UV source 68. Source 66 has an emission aperture which is optically aligned (along optical axis 69) with bandpass filter (BPF) 70 and lens 72. Similarly, source 68 has an emission aperture which is optically aligned (along optical axis 73) with bandpass filter (BPF) 74 and lens 76.

In one mode of the invention, applicator 52 functions both as a fluoresence detector and a UVA transmitter. In accordance with such mode, and as depicted by arrow 78 in FIG. 1, the positions of sources 66 and 68 can be selectively alternated so that (at any one time) either optical axis 69 or optical axis 73 is aligned whereby rays from a respective one of the sources 66, 68 are incident upon end 55a of optical fiber sub-bundle 54a. Alternatively, end 55a of optical fiber sub-bundle 54a can be selectively aligned with either optical axis 69 or optical axis 73.

In another mode of the invention, applicator 52 serves as a fluoresence detector and applicator 152 serves as a UVA transmitter.

Detection station 60 includes an optical receiver 80 and a computer 86. Optical receiver 80 includes a spectrograph 82 and an optical multi-channel analyzer (OMA) 84. Computer 86 is connected to output terminals of OMA 84 in conventional fashion. An input window of spectrograph 82 is aligned on an optical axis 90 with end 55b of optical fiber sub-bundle 54b. Bandpass filter 92 and coupling lens 94 lie on axis 90 between fiber end 55b and spectrograph 82.

As used herein, the term "applicator" can also mean a probe or catheter suitable for being fitted to or for housing optical fiber bundles 54 and/or 154. Differing embodiments of optical fiber bundles 54a, 54b, and 54c are illustrated in the end views of FIGS. 3A, 3B, and 3C, respectively. In the FIG. 3A embodiment, bundle 54a has a covering 56a through which extend one excitation fiber 102a and one detection fiber 104a. In the FIG. 3B embodiment, bundle 54b has one excitation fiber 102b and a plurality (e.g., four) detection fibers 104b. In the FIG. 3C embodiment, bundle 54c has a plurality of excitation fibers 102c and a plurality of detection fibers 104c. Since applicator 152 is used only for UVA excitation or transmission, bundle 154 typically contains only excitation fibers, of which there may be a plurality in arrangements comparably configured with FIGS. 3A, 3B, and 3C, for example.

Figure 2:
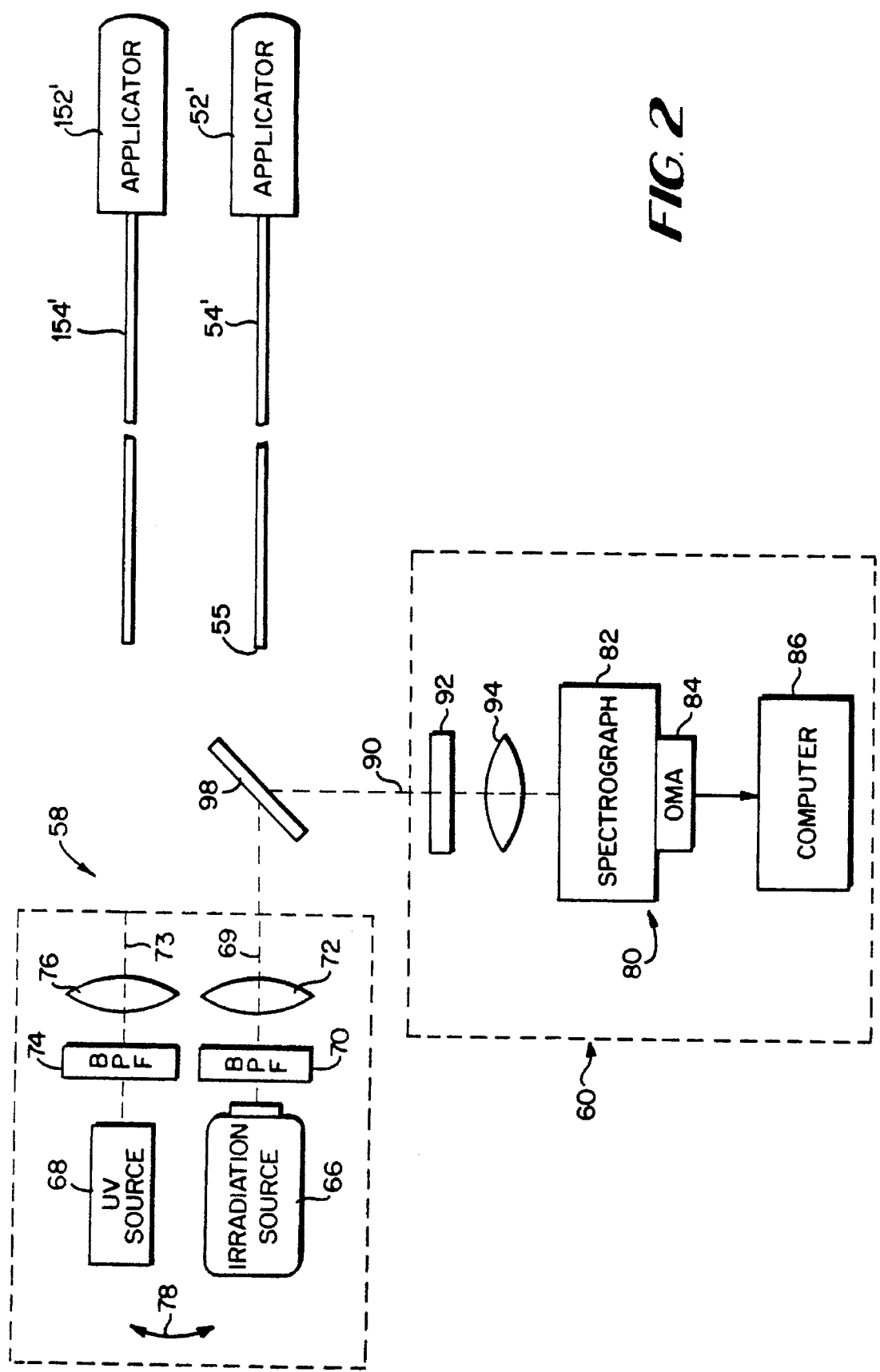
FIG. 2 is a schematical diagrammatic view of a system for in vivo determination of psoralen levels and UV treatment according to a second (single optical fiber) embodiment of the invention.

FIG. 2 shows a psoralen concentration determination and UV treatment system 50' according to a second embodiment of the invention. System 50' includes an in vivo applicator 52' fitted on an end of an optical fiber bundle 54'. System 50' of FIG. 2 has launching station 58 and detection station 60, which (other than physical positioning of the detection station 60) are essentially the same as the respective stations for system 50 of FIG. 1.

System 50' of FIG. 2 differs from system 50 of FIG. 1 in that optical fiber bundle 54' consists of a single optical fiber (either single mode or multi-mode, coherent or incoherent). Further, system 50' differs in that end 55' of fiber bundle 54' is optically aligned with a dichroic mirror 98. Rays incident on dichroic mirror 98 from launching station 58 (whether from source 66 or source 68) are transmitted through mirror 98 to optically-aligned end 55' of bundle 54'. Rays exiting from end 55' of bundle 54' are reflected along optical axis 90 to detection station 60.

Describing now in more detail various components of the foregoing embodiments, the source 66 can be of several types, including either arc lamp or laser. Preferably, source 66 emits a wavelength in a range of from 340 nm to about. 400 nm. In an arc lamp embodiment, an ORIEL model #60005 lamp is used with an ORIEL 100 W Hg model #6281 bulb.

Source 68 can be a laser, such as a doubled titanium-sapphire laser, an ultraviolet argon laser, or a frequency-doubled diode laser. A single appropriate laser may, in an alternate embodiment, serve as both source 66 and source 68, thereby obviating the interchanging of two sources.

Spectrograph 82 and OMA 84 can be any of several conventional models, including EG&G Model #1232 spectrograph and an EG&G Model #1460 Optical Multi-channel Analyzer. In conventional manner, optical receiver 80 includes a gated detector, such as EG&G Model #1420.

FIGS. 4-7 show differing embodiments of applicators for differing biological targets. As described below, the target can be serum (e.g., blood), blood vessels, skin, or other tissue. It should be understood that, although optical fiber bundle OFB is generically indicated in FIGS. 4-7, the applicators of FIGS. 4-7 could (unless otherwise stated or evident from the context) utilize any of the optical fiber bundles 54a–54c of FIGS. 3A–3C, respectively; optical fiber bundle 154; or optical fiber bundle 54' of FIG. 2.

FIG. 4 shows an applicator 452 used for in vivo determination of psoralen concentrations in serum (e.g., blood). Applicator 452 is essentially a terminal end of optical fiber bundle OFB. The particular optical fiber bundle OFB illustrated in FIG. 4 happens to be bundle 54a of FIG. 3A, which includes excitation fiber 102a and detection fiber 104a. As shown, applicator 452 is positioned in an interior channel of a blood vessel BV.

FIG. 5 shows a combined optical and saline flush delivery system 400 used for in vivo determination of psoralen concentrations in a blood vessel wall BVW, including an applicator 552. FIG. 5A is an enlarged view of a distal end of applicator 552. Applicator 552 is essentially a conventional catheter 553 of sufficient inner diameter to permit both insertion of optical fiber bundle OFB and a saline flush (the flow of the flush being depicted by arrows 560). In use, applicator 552 is positioned so that a distal end thereof is slightly spaced away from the blood vessel wall BVW, thereby allowing incidence of the irradiation and flow of the saline flush (as indicated arrows 560).

A proximal end of catheter 533 is received in a female luer taper 570 formed at a downstream end of Y-adapter 574. Branched leg 576 of Y-adapter 574 receives the saline flush. An upstream end of Y-adapter 574 has a fitting through which extends optical fiber bundle OFB and which receives a first end 580 teflon protective covering 582. A second end 584 of teflon protective covering 582 is engaged by SMA connector 590. An end 592 of optical fiber bundle OFB extends through SMA connector 590 for connection to the source in launching station 58.

FIG. 6A and FIG. 6B show applicators 652A and 652B used for determination of psoralen concentrations in skin (SK). Applicators 652A and 652B are also known as skin probes. Applicators 652A and 652B include a fiber holder 670 having a cylindrical section 672 and a ring-shaped foot section 674. The major axis of cylindrical section 672 extends orthogonally with respect to the surface of the skin SK. The underside of foot section 674 is relatively flat for abutting the surface of the skin SK. The inner diameter of cylindrical section 672 (represented by arrow 676) is on the order of about 1 centimeter; the outer diameter of foot section 674 (depicted by arrow 678) in on the order of about 3 centimeters; the thickness of foot section 674 (depicted by arrow 680) is on the order of about 3 millimeters. The applicators 652A and 652B may be formed from any rigid material such as metal or plastic. Preferably the internal surface of cylindrical section 670 is coated with a highly reflective white paint (e.g., $BaSO_4$).

Internally formed or fitted in cylindrical section 672 is a spline or retaining ring 682 which engages optical fiber bundle OFB. In applicator 652A (shown in FIG. 6A), optical fiber bundle OFB is engaged by retaining ring 682 so that the distal end of optical fiber bundle OFB will be flush against the surface of the skin SK. In applicator 652B (shown in FIG. 6B), on the other hand, retaining ring 682B is more greatly spaced apart from the surface of skin SK and engages the distal end of optical fiber bundle OFB (e.g., the distal end of optical fiber bundle OFB is essentially flush with the underside of retaining ring 682B). The distance 690 spacing retaining ring 682B from the surface of skin SK is determined by the numerical aperture of the optical fiber bundle OFB.

FIG. 7 shows an applicator 752 used for determination of psoralen concentrations in tissue (e.g, tissue surrounding a blood vessel wall) BVW. Applicator 752 is part of a light delivery and detection system which includes a transparent balloon BA. In the region of tissue requiring psoralen determination, the covering 56 and cladding are removed from optical fiber bundle OFB (preferably a single fiber) to facilitate light transmission to and from the tissue T. Irradiation light conducted along optical fiber bundle OFB is, at the region of covering-removed fiber, scattered laterally (e.g., essentially perpendicular to the main axis of the fiber bundle OFB) and exits through the transparent balloon BA into the surrounding target tissue T. Conversely, light emitted by the surrounding target tissue T may enter applicator 752 through the balloon BA, and be deflected into the covering-removed optical fiber bundle OFB for conduction to detection station 60. Embodiments shown in U.S. patent application Ser. No. 08/002,865, filed on 15 Jan. 1993 by GREGORY et al. and entitled ILLUMINATOR DEVICES FOR ULTRAVIOLET LIGHT DELIVERY AND METHODS OF MAKING SAME (incorporated herein by reference) are suitable for use as applicators for the embodiment of FIG. 7.

FIG. 9 shows a portable psoralen concentration determination system 950. Portable system 950 is mounted on a mobile (e.g., wheeled) cart 920. Cart 920 has a top surface 922 and two shelves including bottom shelf 924 and middle shelf 926. Portable system 950 includes a sample holder 930 positioned on cart top surface 922. Sample holder 930 is adapted to support a sample container such as cuvette 932, for example. Sample holder 930 may alternatively be configured, for example to support a sample-containing dish.

System 950 of FIG. 9 has an applicator 952 fitted on a remote end of optical fiber bundle 954. As with the FIG. 1 embodiment, for example, optical fiber bundle 954 includes two sub-bundles 954a and 954b, with optical fiber sub-bundle 954a having an end 955a which extends toward a launching station 958 and sub-bundle 954b having an end 955b which extends toward a detection station 960.

Applicator 952 can be an optical fiber bundle similar to those already illustrated suitable for contact with a sample container or skin surface. Alternatively, applicator 952 can be configured for immersion in serum (e.g., serum contained in a sample-containing dish).

Launching station 958 includes irradiation source 966 positioned on shelf 926. Irradiation source 966 emits radiation which is incident on end 955a of sub-bundle 954a. The types of sources 66 described with reference to preceding embodiments are appropriate for source 966 of system 950.

As in the FIG. 1 embodiment, detection station 960 includes a spectrograph 982 and OMA 984. OMA 984 is connected to computer 986 (on bottom shelf 924). Computer 986 is connected to a keyboard 988 and a display 990 (both situated on cart top surface 922).

Conveniently, cart 920 can also carry UV source 968 which is employed for emitting UVA to treat a treatment target. Although not shown as such in FIG. 9, UV source 968 is understood to be connectable to an optical fiber bundle and applicator such as bundle 154 and applicator 152 of FIG. 1. Further, UV source 968 may also be used for (e.g., in lieu of) source 966 when appropriate.

FIG. 10 shows a psoralen concentration determination system 1050 according to another embodiment of the invention. In system 1050, an optical fiber bundle 1054 extends from irradiation source 1066 and through a transparent integrating sphere 1020 to a capillary tube 1032. Capillary tube is insertable in sphere 1020. Light detectors 1040A and 1040B optically abut the outer periphery of sphere 1020 and two spaced-apart locations. Each detector 1040 has a filter 1042 associated therewith, and is connected to detection station 1060. Detection station 1060 includes amplifier 1082 and an analog to digital converter 1084, as well as computer (e.g., processor) 1086.

In the embodiment illustrated in FIG. 10, irradiation source 1066 is a pumped dye nitrogen laser (wavelength of 365 nm). Alternatively, other irradiation sources (e.g., arc lamp) can be employed and used, if necessary, in conjunction with optical bandpass filters (e.g., 470±20 nm for the fluorescence signal and 700±20 nm for baseline) interposed between the source and tube 1032. Detectors 1040 include diode arrays. Filters 1042 are provided to eliminate any 365 nm excitation light (e.g., nitrogen laser excitation light) received by detectors 1040. After the source 1066 is triggered, signals collected by the photodiodes of detectors 1040 are collected during irradition by source 1066.

FIG. 8 shows steps involved in methods of the invention. It should be understood that the methods depicted by FIG. 8 can be executed in either of two modes. In a first mode, psoralen concentration for a subject is determined with reference to an actual biological target (e.g., treatment target) which eventually is to be treated with the PUVA therapy. In such first mode, an applicator is situated/installed proximate tissue which serves both as a detection target and a treatment target. In a second mode, tissue (e.g., blood) is extracted from the subject to serve as a detection target and is placed in an appropriate in vitro container. Psoralen concentration is determined by positioning a first applicator (e.g., applicator 52 in FIG. 1) proximate the container, and then emitting the appropriate amount of UVA using a second applicator (e.g., applicator 152 in FIG. 1) positioned/installed proximate the treatment target. Thus, in the first mode, the detection target and the treatment target can be one and the same, which is not the case for the second mode. Unless otherwise stated, the steps of FIG. 8 are discussed generically below without regard to mode.

Step 800 involves placement/installation of the applicator with respect to the biological detection target. As explained above, the detection target can be any phyisological component including serum, blood and its components, a blood vessel wall, skin, or other tissue (e.g., tissue surrounding a blood vessel; organs including transplanted organs). Depending on the identity of the target, an appropriate one of the applicators (described with reference to FIGS. 4–10, for example) is employed. Hence, for an in vivo usage, installation of an applicator may be as straightforward as placement of applicator 652A on a surface of skin SK (for example), or on the other hand may be a more intricate procedure such as involving insertion of a balloon BA in connection with applicator 752. For an in vitro/ex vivo usage as shown in FIG. 9 or FIG. 10, step 800 involves placement of the end of optical fiber bundle 954/1054 proximate holder 932 or tube 1032.

After installation/placement of the appropriate applicator, at steps 802 and 804 optical autofluoresence from the detection target is determined. As used herein, optical autofluoresence refers collectively to the fluorescence and/or reflection from an irradiated detection target prior to administering of the psoralen. In particular, at step 802 the detection target is irradiated with light from source 66. Step 802 occurs prior to administering of the psoralen. Preferably the irradiation light has an excitation wavelength in a range from about 340 to about 400, and is more preferably about 365 nm. At step 804, the optical autofluoresence is analyzed at detection station 60 (to which the autofluoresence signal is transmitted by optical fiber bundle 54). The autofluoresence signal is monitored at detection station 60, preferably in a range of 400 nm to 700 nm.

Preferably steps 802 and 804 are repeated to obtain a plurality of readings, from which a mean reading can be taken and utilized as a baseline optical return. Although the behavior of the optical autofluoresence signal differs somewhat depending on the identity of the detection target, a typical optical autofluoresence signal is depicted by curve 900 in FIG. 11A. In FIG. 11A (and also in FIG. 11B discussed subsequently), the ordinate is in units of wavelength (nm) and the abscissa gauges fluorescence/reflectance (counts corresponding to millivolts).

At step 806 a first dosage of psoralen is administered to the subject having the treatment target. Preferably the administered psoralen is 8-methoxypsoralen (8-MOP). The psoralen may be applied either orally, intravenously, or anteriorly (e.g., rectally, e.g., by suppository). As well known, the psoralen dosage level will depend upon a number of factors, including the nature of the tissue and attributes of the patient.

After administration of psoralen, irradiation of the detection target occurs at step 808. As mentioned above, the irradiation of step 808 may be irradiation of an actual biological target (e.g., treatment target) which eventually is to be treated with the PUVA therapy, or some other tissue (e.g., blood) extracted from the subject to serve as a detection target. In the latter case, a sample holder is filled with tissue (e.g., blood) extracted after administration of psoralen. In either case, the irradiation at step 808 is conducted with the same conditions (e.g., same wavelength) as the pre-psoralen irradiation of step 802.

Then, at step 810, the optical return from the psoralen-treated detection target is analyzed at a detection station such as station 60 of FIG. 1. As used herein, optical return refers collectively to fluorescence and/or reflection, and at step 810 in particular refers to the fluorescence and/or reflection from an irradiated detection target treated with psoralen. Again, the optical return signal will vary according to peculiarities of the subject/target. The optical return signal is monitored at the detection station in the same range as the autofluoresence signal (e.g., preferably in a range of 400 nm to 700 nm). Curve 902 of FIG. 11A depicts a typical optical return signal from an irradiated detection target treated with psoralen.

Curve 902 differs from curve 900 in view of the fact that psoralen absorbs light and can fluoresce. The absorption of psoralen changes the reflectance of the target and the fluorescence of the target changes. As explained below, these changes are used to quantify the psoralen levels in the target.

At step 812, a computer 86 of the detection system (e.g., computer 86 of the detection system 60 of FIG. 1) compares the pre-psoralen optical return (taken from step 804) and psoralen-treated optical return (taken from step 810) to calculate a real time determination of the concentration level of psoralen in the detection target. According to one mode of conducting the calculation of step 810, the readings obtained at step 804 are subtracted from the readings obtained at step 810. While the calculation of this mode of step 812 can take many forms, a simple technique is to determine the area between curves 902 and 900 of FIG. 11A using conventional programmed instructions. Curve 904 of FIG. 11B represents the result of such a difference calculation undertaken with respect to curves 900 and 902 of FIG. 11A. Curve 904 is a signature of psoralen. By taking the area beneath curve 904, the level of psoralen concentration in the target can readily be determined. According to another mode, at a plurality of wavelengths florescence ratios are formed. For example, referring again to FIG. 11A, the ratio of fluorescence yields at 450 nm and 500 nm provide a measure of psoralen concentration of the target.

At step 814 a determination is made whether the detection target has ingested or otherwise contains a sufficient concentration of psoralen. In a fully automated system, a computer or processor (such as computer 86) can make the determination of step 814 if provided with sufficient information, including the nominal or desired UV dosage level. If there is an insufficient concentration of psoralen, at step 814 the computer can prompt for a further administering of psoralen (step 816), and may even compute the needed psoralen dosage amount.

If the level of psoralen concentration is determined at step 814 to be sufficient, then knowing the precise psoralen concentration level, at step 818 the computer determines the necessary UV dosage level required to achieve the desired PUVA therapy. With the UV dosage level thusly determined, UV energy from a UV source (e.g., source 68) is then applied by an appropriate applicator to the treatment target. In a fully automated system, operation (and relocation, if necessary) of UV source 68 is under control of computer 86.

Alternatively, based on the computer-obtained determination of step 812, a human attendant may make the determinations of step 814 and/or step 818 and activate an appropriate UV source [e.g., UV source 68] (at step 820).

In view of the foregoing discussion, it should be understood that, application of the UV light (e.g., from source 68) can occur in a first mode of the invention using the same applicator which was involved in the psoralen concentration determination (e.g., applicator 52 of FIG. 1). In the second mode of the invention, the UV light is applied with a second and distinct applicator (e.g., applicator 152 of FIG. 1).

While the invention has been particularly shown and described with reference to the preferred embodiments thereof, it will be understood by those skilled in the art that various alterations in form and detail may be made therein without, departing from the spirit and scope of the invention.

The embodiments of the invention in which an exclusive property or privilege is claimed are defined as follows:

1. A method of determining psoralen concentration prior to application of PUVA therapy, the method comprising:
   (1) optically exciting a biological detection target whereby the excited detection target fluoresces;
   (2) obtaining a fluorescence spectrum from the optically excited detection target;
   (3) using the fluorescence spectrum to determine psoralen concentration in the optically excited detection target.

2. The method of claim 1, wherein the step of obtaining a fluorescence spectrum includes obtaining a pre-psoralen fluorescence spectrum before the optically excited target contains psoralen and a post-psoralen fluorescence spectrum after the optically excited target contains psoralen.

3. The method of claim 1, further comprising:
   (4) determining, in accordance with the determination of step (3), a dosage level of ultraviolet radiation for application to a biological treatment target.

4. The method of claim 3, wherein the treatment target is tissue selected from a group consisting of serum, blood and its components, a blood vessel wall, skin, or other tissue surrounding a blood vessel.

5. The method of claim 3, wherein the detection target and the treatment target are the same.

6. The method of claim 3, wherein the detection target is tissue selected from a group consisting of serum, blood and its components, a blood vessel wall, skin, or other tissue surrounding a blood vessel.

7. The method of claim 3, further comprising:
   (5) applying the dosage level of step (4) to the biological treatment target.

8. The method of claim 1, wherein the step of optically exciting the detection target comprises irradiating the detection target with a first end of an optical fiber, a second end of the optical fiber being coupled to a source of irradiation.

9. The method of claim 1, wherein the step of optically exciting the detection target comprises using a source of irradiation to emits a range of excitation wavelengths.

10. The method of claim 9, wherein the source of irradiation emits a wavelength in a range on the order of from about 350 nm to about 400 nm.

11. The method of claim 10, wherein the source of irradiation emits a wavelength of about 365 nm.

12. The method of step 1, further comprising transmitting radiation reflected and/or fluoresced from the detection target via an optical fiber to a detector.

13. The method of claim 12, further comprising using the detector to monitor the change in fluorescence in a wavelength range from about 400 nm to about 700 nm.

14. The method of claim 1, wherein the detection target is in vivo tissue.

15. A method of treating a biological treatment target using PUVA therapy, the method comprising:
   (1) administering psoralen to a biological detection target;
   (2) determining in vivo and in real time a concentration level of the psoralen in the detection target;
   (3) determining, in accordance with the determination of step (2), a dosage level of ultraviolet radiation for application to the treatment target; and
   (4) applying the dosage level of step (3) to the treatment target.

16. The method of claim 15, wherein the step of determining the concentration level of the psoralen in the target comprises:
   optically exciting the detection target;
   contrasting the optical reflectance and/or fluorescence of
   (a) the detection target with psoralen administered with
   (b) the detection target without psoralen.

17. The method of claim 16, wherein the step of optically exciting the detection target comprises irradiating the detection target with a first end of an optical fiber, a second end of the optical fiber being coupled to a source of irradiation.

18. The method of claim 15, wherein the detection target and the treatment target are the same.

19. The method of claim 15, wherein the detection target is tissue selected from a group consisting of serum, blood and its components, a blood vessel wall, skin, or other tissue.

20. The method of claim 15, wherein the step of determining the concentration level of the psoralen in the detection target comprises irradiating the detection target with a first end of an optical fiber, a second end of the optical fiber being coupled to a source of irradiation.

21. The method of claim 15, wherein step (2) involves optically exciting the detection target using a source of irradiation which emits a range of excitation wavelengths.

22. The method of claim 21, wherein the source of irradiation emits a wavelength in a range on the order of from about 350 nm to about 400 nm.

23. The method of claim 22, wherein the source of irradiation emits a wavelength of about 365 nm.

24. The method of claim 15, further comprising transmitting radiation reflected and/or fluoresced from the detection target via an optical fiber to a detector.

25. The method of claim 24, further comprising using the detector to monitor the change in fluorescence in a wavelength range from about 400 nm to about 700 nm.

26. The method of claim 15, wherein the step of administering psoralen comprises administering psoralen to in vivo tissue.

27. A method of treatment of an in vivo biological treatment target using PUVA therapy, the method comprising:

(1) administering psoralen to the treatment target undergoing therapy;

(2) optically exciting the treatment target by irradiating the target with radiation from a first end of an irradiating optical fiber, a second end of the irradiating optical fiber being coupled to a source of excitation irradiation;

(3) using a receptor optical fiber to transmit optical reflectance and/or fluorescence of the in vivo treatment target to a detector coupled to second end of the receptor optical fiber;

(4) using the optical reflectance and/or fluorescence of the in vivo target to determine in real time a concentration level of the psoralen in the treatment target;

(5) determining, in accordance with the determination of step (4), a dosage level of ultraviolet radiation for application to the treatment target; and (6) applying the dosage level of step (5) to the treatment target using the same optical fiber used to excite the treatment target.

28. The method of claim 27, wherein the source of irradiation emits a range of excitation wavelengths.

29. The method of claim 28, wherein the source of irradiation emits a wavelength in a range on the order of from about 350 nm to about 400 nm.

30. The method of claim 29, wherein the source of irradiation emits a wavelength of about 365 nm.

31. The method of claim 27, wherein the detector monitors the change in fluorescence in a wavelength range from about 400 nm to about 700 nm.

32. Apparatus for determining psoralen concentration prior to application of PUVA therapy, the apparatus comprising:

a source of excitation energy;

means for applying the excitation energy to a biological detection target and thereby causing the detection target to fluoresce;

means for detecting the fluorescence of the excited detection target and obtaining a fluorescence spectrum from the excited detection target;

means for using the fluorescence spectrum to determine psoralen concentration in the optically excited detection target.

33. The apparatus of claim 32, wherein means for determining psoralen concentration obtains a pre-psoralen fluorescence spectrum before the optically excited target contains psoralen and a post-psoralen fluorescence spectrum after the optically excited target contains psoralen.

34. The apparatus of claim 32, further comprising:

means for determining, in accordance with psoralen concentration, a dosage level of ultraviolet radiation for application to a biological treatment target; and means for applying the dosage level of step to the biological treatment target.

35. The apparatus of claim 32, further comprising an optical fiber bundle comprising an optical fiber connected to transmit radiation from the source of excitation energy to the detection target.

36. The apparatus of claim 32, wherein the source of excitation energy emits a range of excitation wavelengths.

37. The apparatus of claim 36, wherein the source of excitation energy emits a wavelength in a range on the order of from about 350 nm to about 400 nm.

38. The apparatus of claim 37, wherein the source of excitation energy emits a wavelength of about 365 nm.

39. The apparatus of claim 32, further comprising an optical fiber bundle comprising an optical fiber connected to transmit radiation reflected and/or fluoresced from the detection target via an optical fiber to a detector.

40. The apparatus of claim 39, wherein the detector monitors the change in fluorescence in a wavelength range from about 400 nm to about 700 nm.

41. The apparatus of claim 32, wherein the means for applying the excitation energy to the detection target comprises means for applying the excitation energy to in vivo tissue.

42. The apparatus of claim 32, further comprising a mobile cart, and wherein the source of excitation energy; the means for applying the excitation energy; the means for detecting the fluorescence of the excited detection target and obtaining a fluorescence spectrum; and the means for determining psoralen concentration in the optically excited detection target are all mounted on the mobile cart.

43. The apparatus of claim 32, wherein the biological detection target is positioned in an optically integrating sphere.

44. A method of treating a biological treatment target using PUVA therapy, the method comprising:

(1) administering psoralen to a biological detection target;

(2) determining in vivo and in real time a concentration level of the psoralen in the detection target;

(3) using a processor to determine, in accordance with the determination of step (2), a dosage level of ultraviolet radiation for application to the treatment target; and (4) automatically applying the dosage level of step (3) to the treatment target.

45. Apparatus for determining psoralen concentration prior to application of PUVA therapy, the apparatus comprising:

a source of excitation energy;

means for applying the excitation energy to a biological detection target and thereby causing the detection target to fluoresce;

means for detecting the fluorescence of the excited detection target and obtaining a fluorescence spectrum from the excited detection target;

a processor which uses the fluorescence spectrum to determine psoralen concentration in the optically excited detection target and to determine, in accordance with psoralen concentration, a dosage level of ultraviolet radiation for application to a biological treatment target; and means for automatically applying the dosage level of step to the biological treatment target.

* * * * *